(12) United States Patent
Taninai et al.

(10) Patent No.: US 12,205,284 B2
(45) Date of Patent: Jan. 21, 2025

(54) IMAGE PROCESSING DEVICE, MOBILE MEDICAL IMAGING APPARATUS, IMAGE PROCESSING METHOD, AND IMAGE PROCESSING PROGRAM

(71) Applicant: FUJIFILM CORPORATION, Tokyo (JP)

(72) Inventors: Koji Taninai, Kanagawa (JP); Hiromu Hayashi, Kanagawa (JP); Akihito Bettoyashiki, Kanagawa (JP); Takeyasu Kobayashi, Kanagawa (JP); Kazuhiro Makino, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 294 days.

(21) Appl. No.: 17/744,768

(22) Filed: May 16, 2022

(65) Prior Publication Data

US 2022/0375075 A1 Nov. 24, 2022

(30) Foreign Application Priority Data

May 19, 2021 (JP) ................................ 2021-084860

(51) Int. Cl.
*G06T 7/00* (2017.01)
*A61B 6/00* (2006.01)

(52) U.S. Cl.
CPC .......... *G06T 7/0012* (2013.01); *A61B 6/4405* (2013.01); *A61B 6/5205* (2013.01);
(Continued)

(58) Field of Classification Search
CPC ......... G06T 7/0012; G06T 2207/20132; G06T 2207/30096; A61B 6/4405; A61B 6/5205;
(Continued)

(56) References Cited

U.S. PATENT DOCUMENTS

2017/0323447 A1\* 11/2017 Tsukagoshi ............ A61B 6/467
2018/0368797 A1 12/2018 Kuwata et al.
(Continued)

FOREIGN PATENT DOCUMENTS

JP 2002-112986 A 4/2002
JP 2017-202310 A 11/2017
(Continued)

OTHER PUBLICATIONS

English language translation of the following: Office action dated Nov. 26, 2024 from the JPO in a Japanese patent application No. 2021-084860 corresponding to the instant patent application. This office action translation is submitted now in order to supplement the understanding of the cited references which are being disclosed in the instant Information Disclosure Statement.

*Primary Examiner* — Ping Y Hsieh
*Assistant Examiner* — Vaisali Rao Koppolu
(74) *Attorney, Agent, or Firm* — SOLARIS Intellectual Property Group, PLLC

(57) ABSTRACT

A console includes a CPU that acquires an image to be processed which is an object to be subjected to a support process that is a diagnosis support process or an imaging support process and selects a support process to be applied to the image to be processed from a plurality of processes of the support process on the basis of a part of a subject which is included in the image to be processed.

7 Claims, 6 Drawing Sheets

(52) U.S. Cl.
CPC .............. *G06T 2207/20132* (2013.01); *G06T 2207/30096* (2013.01)

(58) Field of Classification Search
CPC ....... A61B 6/06; A61B 6/4441; A61B 6/5211; A61B 6/4208; A61B 6/505; A61B 6/54
See application file for complete search history.

(56) References Cited

U.S. PATENT DOCUMENTS

| | | |
|---|---|---|
| 2019/0150857 A1 | 5/2019 | Nye et al. |
| 2019/0156484 A1 | 5/2019 | Nye et al. |
| 2019/0164285 A1* | 5/2019 | Nye ........................ G16H 10/60 |
| 2020/0250860 A1* | 8/2020 | Son .......................... A61B 6/54 |
| 2020/0372651 A1 | 11/2020 | Nye et al. |
| 2021/0015433 A1 | 1/2021 | Nye et al. |
| 2021/0342195 A1 | 11/2021 | Kudo |
| 2022/0198663 A1 | 6/2022 | Harada |

FOREIGN PATENT DOCUMENTS

| | | |
|---|---|---|
| JP | 2019-005073 A | 1/2019 |
| JP | 2019-93137 A | 6/2019 |
| WO | 2020/158100 A1 | 8/2020 |
| WO | 2021/049478 A1 | 3/2021 |

\* cited by examiner

IMAGE PROCESSING DEVICE, MOBILE MEDICAL IMAGING APPARATUS, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2021-084860, filed on May 19, 2021. The above application is hereby expressly incorporated by reference, in its entirety, into the present application.

BACKGROUND

1. Technical Field

The present disclosure relates to an image processing device, a mobile medical imaging apparatus, an image processing method, and an image processing program.

2. Description of the Related Art

A technique is known which executes a diagnosis support process for medical images such as radiographic images. For example, JP2019-93137A describes a technique that applies a trained learning network to a captured image and notifies a user in a case in which clinical findings are seen.

SUMMARY

However, there are various types of medical images, and the diagnosis support process to be applied may differ depending on the type of medical image. Therefore, in some cases, an operator may be burdened with, for example, selecting a diagnosis support process in order to apply an appropriate diagnosis support process corresponding to the type of medical image.

The present disclosure has been made in view of the above circumstances, and an object of the present disclosure is to provide an image processing device, a mobile medical imaging apparatus, an image processing method, and an image processing program that can reduce a burden on an operator.

In order to achieve the above object, according to a first aspect of the present disclosure, there is provided an image processing device comprising at least one processor. The processor acquires an image to be processed which is an object to be subjected to a support process that is a diagnosis support process or an imaging support process, and selects a support process to be applied to the image to be processed from a plurality of processes of the support process on the basis of a part of a subject which is included in the image to be processed.

According to a second aspect of the present disclosure, in the image processing device according to the first aspect, the processor may apply the selected support process to the image to be processed and output a support process result.

According to a third aspect of the present disclosure, in the image processing device according to the first aspect or the second aspect, a priority may be set for the support process. In a case in which a plurality of support processes are applied to the image to be processed, the processor may apply the support processes to the image to be processed in an order based on the priority.

According to a fourth aspect of the present disclosure, in the image processing device according to any one of the first to third aspects, the processor may execute the support process for each of a plurality of lesions according to the part and present the support process results in an order based on the priority set for the plurality of lesions.

According to a fifth aspect of the present disclosure, in the image processing device according to any one of the first to fourth aspects, the processor may trim the image to be processed on the basis of the part and apply the support process to the trimmed image to be processed.

In order to achieve the above object, according to a sixth aspect of the present disclosure, there is provided a mobile medical imaging apparatus comprising: the image processing device according to the present disclosure; and a power source that supplies power to the processor of the image processing device.

In order to achieve the above object, according to a seventh aspect of the present disclosure, there is provided an image processing method that is executed by a computer. The image processing method comprises: acquiring an image to be processed which is an object to be subjected to a support process that is a diagnosis support process or an imaging support process; and selecting a support process to be applied to the image to be processed from a plurality of processes of the support process on the basis of a part of a subject which is included in the image to be processed.

In order to achieve the above object, according to an eighth aspect of the present disclosure, there is provided an image processing program that causes a computer to execute a process comprising: acquiring an image to be processed which is an object to be subjected to a support process that is a diagnosis support process or an imaging support process; and selecting a support process to be applied to the image to be processed from a plurality of processes of the support process on the basis of a part of a subject which is included in the image to be processed.

According to the present disclosure, it is possible to reduce a burden on an operator.

BRIEF DESCRIPTION OF THE DRAWINGS

Exemplary embodiments according to the technique of the present disclosure will be described in detail based on the following figures, wherein.

DETAILED DESCRIPTION

Hereinafter, an embodiment of the present disclosure will be described in detail with reference to the drawings. In the following embodiment, an aspect will be described in which a radiographic image is applied as an example of an image to be processed according to the present disclosure and a console of a mobile radiography apparatus is applied as an example of an image processing device according to the present disclosure. In addition, this embodiment does not limit the present disclosure.

Figure 1:
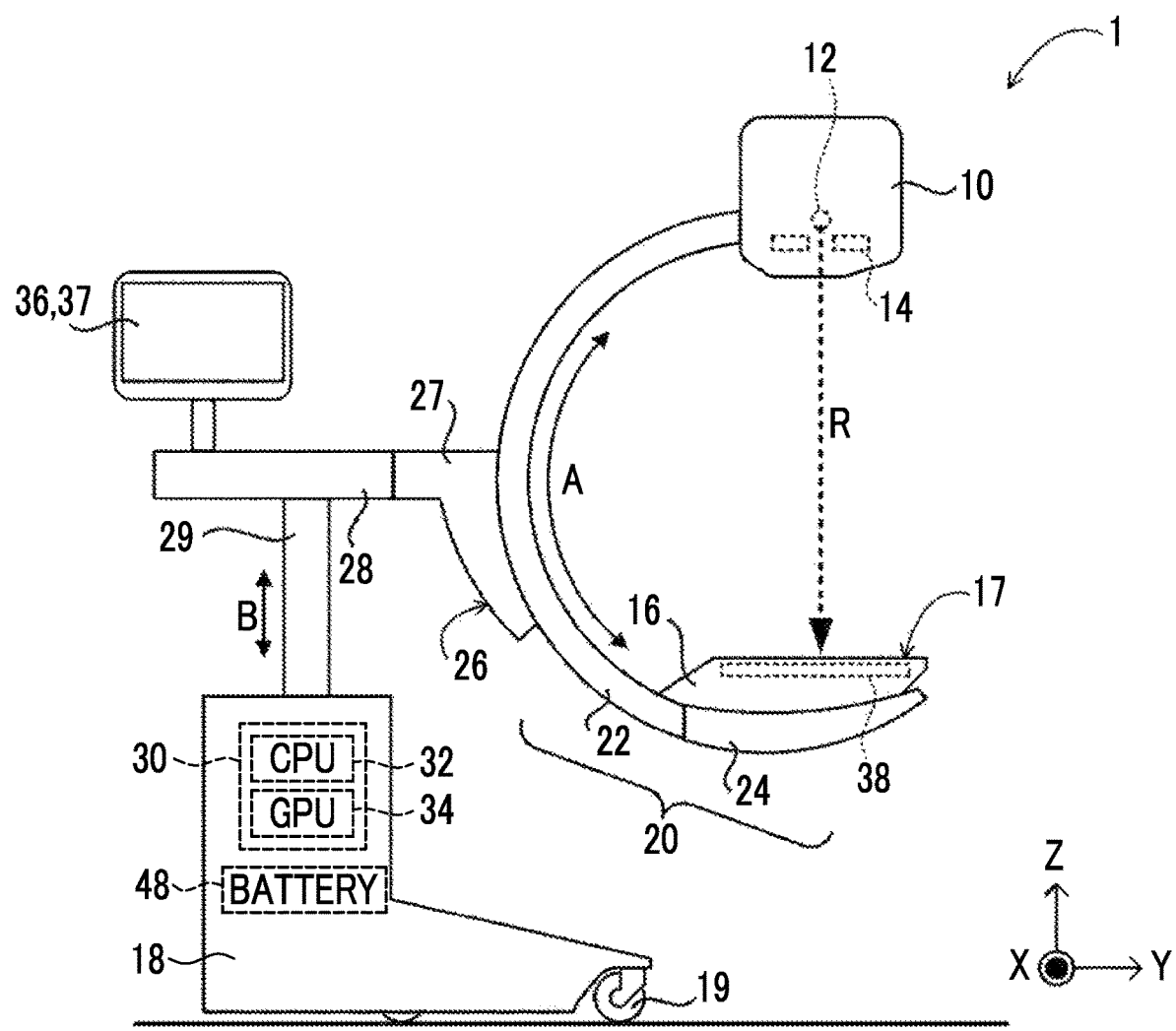
FIG. 1 is a diagram illustrating an example of the overall configuration of a mobile radiography apparatus according to an embodiment.

First, an example of the overall configuration of the mobile radiography apparatus according to this embodiment will be described. FIG. 1 is a diagram illustrating an example of the overall configuration of a mobile radiography apparatus 1 according to this embodiment.

As illustrated in FIG. 1, the mobile radiography apparatus 1 according to this embodiment comprises a C-arm 20 having an arm portion 22 and a holding portion 24. A radiation emitting unit 10 that emits radiation R generated by a radiation source 12 is provided at one end of the arm portion 22.

The radiation source 12 and an irradiation field limiter 14 are accommodated in the radiation emitting unit 10. The radiation source 12 has a radiation tube (not illustrated) that generates the radiation R and has a function of emitting the radiation R generated by the radiation tube. The irradiation field limiter 14 is a so-called collimator that has a function of limiting the irradiation field of the radiation R generated by the radiation tube. For example, the irradiation field limiter 14 has a configuration in which four shielding plates made of lead or the like that shields the radiation R are disposed on each side of a quadrangle and a quadrangular opening portion for transmitting the radiation R is formed in a central portion. The irradiation field limiter 14 changes the position of each shielding plate to change the size of the opening portion, thereby changing the irradiation field of the radiation R.

On the other hand, the holding portion 24 is provided at the other end of the arm portion 22. The holding portion 24 holds an accommodation portion 16. The accommodation portion 16 accommodates a radiation detector 38 that detects the radiation R and generates image data indicating a radiographic image. The C-arm 20 according to this embodiment has a function of changing the angle of the radiation detector 38 with respect to the Z direction (vertical direction) illustrated in FIG. 1.

The radiation detector 38 detects the radiation R transmitted through the subject. Specifically, the radiation detector 38 detects the radiation R that has entered the accommodation portion 16 and reached a detection surface of the radiation detector 38, generates a radiographic image on the basis of the detected radiation R, and outputs image data indicating the generated radiographic image. In the following description, in some cases, a series of operations of emitting the radiation R from the radiation source 12 and generating a radiographic image using the radiation detector 38 is referred to as "imaging". The type of the radiation detector 38 according to this embodiment is not particularly limited. For example, the radiation detector 38 may be an indirect-conversion-type radiation detector that converts the radiation R into light and converts the converted light into charge or a direct-conversion-type radiation detector that directly converts the radiation R into charge. Further, the radiation detector 38 can capture at least one of a still image or a moving image.

An imaging surface 17 irradiated with the radiation R emitted from the radiation emitting unit 10 is provided on a side of the accommodation portion 16 which faces the radiation emitting unit 10. In addition, in the mobile radiography apparatus 1 according to this embodiment, a so-called source to image distance (SID) which is a distance between the imaging surface 17 and the radiation source 12 of the radiation emitting unit 10 is a fixed value.

The C-arm 20 is held by a C-arm holding portion 26 so as to be movable in the direction of an arrow A illustrated in FIG. 1. Further, the C-arm holding portion 26 has a shaft portion 27, and the shaft portion 27 connects the C-arm 20 to a bearing 28. The C-arm 20 is rotatable about the shaft portion 27 as a rotation axis.

Furthermore, as illustrated in FIG. 1, the mobile radiography apparatus 1 according to this embodiment comprises a main body portion 18 that has a plurality of wheels 19 provided at the bottom. A support shaft 29 that is expanded and contracted in the Z-axis direction of FIG. 1 is provided in an upper part of a housing of the main body portion 18 in FIG. 1. The bearing 28 is held in the upper part of the support shaft 29 so as to be movable in the direction of an arrow B.

Further, a display unit 36 and an operation unit 37 are provided in the upper part of the main body portion 18. The display unit 36 and the operation unit 37 function as a user interface. The display unit 36 provides an operator, such as a technician or a doctor, who takes a radiographic image with the mobile radiography apparatus 1 with the captured radiographic image or information related to the capture of the radiographic image. The display unit 36 is not particularly limited. Examples of the display unit 36 include a liquid crystal monitor and a light emission diode (LED) monitor. In addition, in this embodiment, a touch panel display integrated with the operation unit 37 is applied as an example of the display unit 36. Further, the operator operates the operation unit 37 to input an instruction related to the capture of a radiographic image. The operation unit 37 is not particularly limited. Examples of the operation unit 37 include various switches, a touch panel, a touch pen, and a mouse. Furthermore, a plurality of operation units 37 may be provided. For example, a touch panel and a foot switch operated by the operator with his or her feet may be provided as the operation unit 37.

Moreover, the main body portion 18 accommodates, for example, a central processing unit (CPU) 32 and a graphics processing unit (GPU) 34 of a console 30 and a battery 48 that supplies power to each unit of the mobile radiography apparatus 1.

Figure 2:
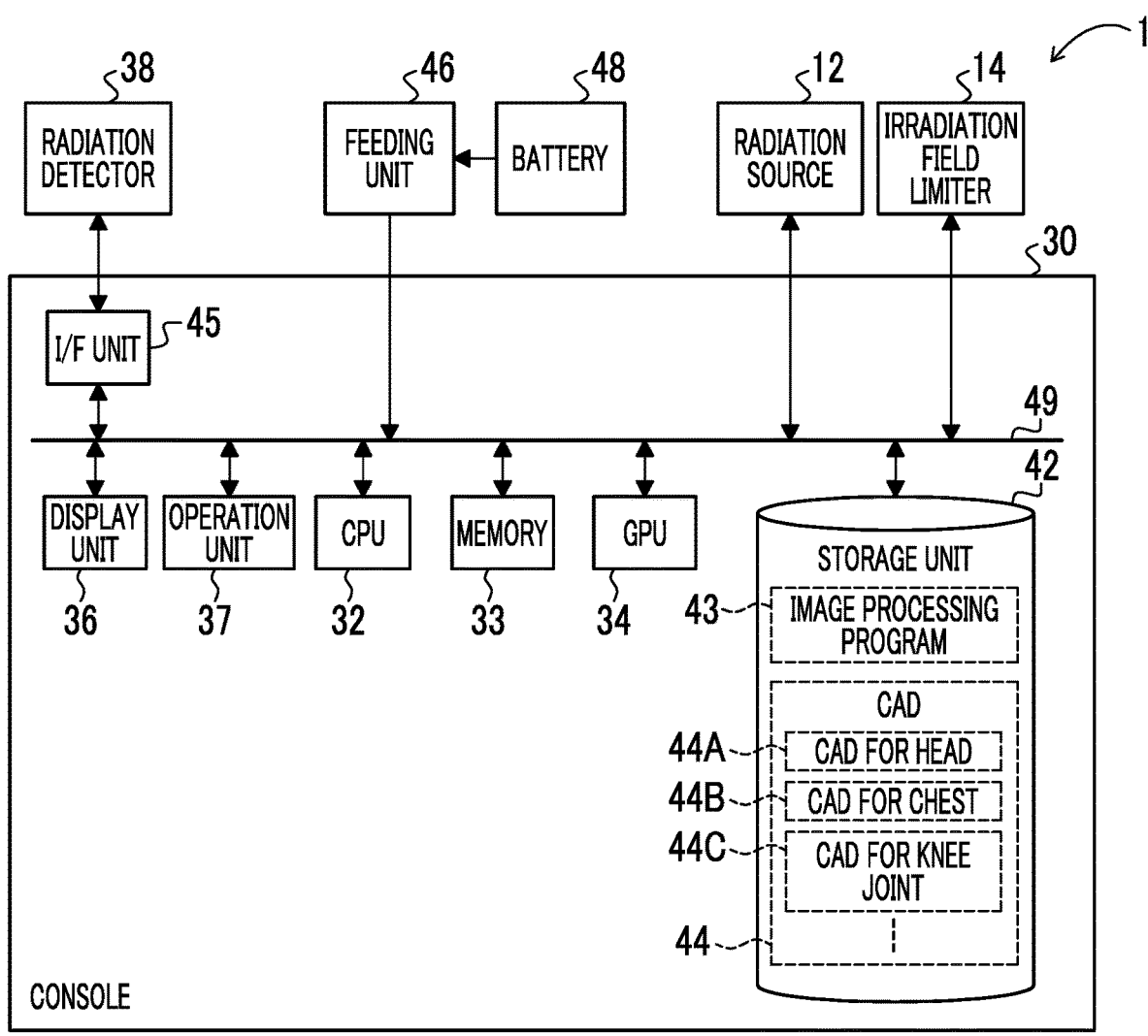
FIG. 2 is a block diagram illustrating an example of the configuration of the mobile radiography apparatus according to the embodiment.

FIG. 2 is a block diagram illustrating an example of the configuration of the mobile radiography apparatus 1 according to this embodiment. As illustrated in FIG. 2, the mobile radiography apparatus 1 according to this embodiment comprises the radiation source 12, the irradiation field limiter 14, the console 30, the radiation detector 38, a feeding unit 46, and the battery 48.

The console 30 has a function of performing control related to the capture of a radiographic image by the mobile radiography apparatus 1. The console 30 according to this embodiment is an example of an information processing device according to the present disclosure.

The console 30 comprises the CPU 32, a memory 33, the GPU 34, the display unit 36, the operation unit 37, a storage unit 42, and an I/F unit 45. The CPU 32, the memory 33, the GPU 34, the display unit 36, the operation unit 37, the storage unit 42, and the I/F unit 45 are connected to each other through a bus 49, such as a system bus or a control bus, such that they can transmit and receive various kinds of information. In addition, the radiation source 12, the irradiation field limiter 14, and the feeding unit 46 are also connected to the bus 49.

The CPU 32 reads out various programs including an image processing program 43 stored in the storage unit 42 to the memory 33 and executes a process corresponding to the read-out program. Therefore, the CPU 32 controls the operation of each unit of the mobile radiography apparatus 1. The CPU 32 according to this embodiment is an example of a processor according to the present disclosure. The memory 33 is a work memory that is used by the CPU 32 to perform processes. The GPU 34 has a function of applying a computer-assisted detection/diagnosis (CAD) 44 stored in the storage unit 42 to execute a diagnosis support process, which will be described in detail below, under the control of the CPU 32.

The storage unit 42 stores, for example, the image processing program 43, the CAD 44 which is an algorithm applied to the diagnosis support process, the image data of the radiographic image captured by the radiation detector 38, and various other kinds of information. The CAD 44 includes various algorithms corresponding to the types of diagnosis support processes which will be described below. For example, the CAD 44 according to this embodiment includes a plurality of types of CAD, such as a CAD 44A for the head, a CAD 44B for the chest, and a CAD 44C for the knee joint, which are applied to the radiographic image in the diagnosis support process. Each of the CAD 44A for the head, the CAD 44B for the chest, and the CAD 44C for the knee joint includes a plurality of types of CAD algorithms, which will be described in detail below. In addition, the algorithms included in the CAD 44 are not limited thereto. A specific example of the storage unit 42 is a hard disk drive (HDD), a solid state drive (SSD), or the like.

The I/F unit 45 transmits and receives various kinds of information to and from the radiation detector 38 using wireless communication or wired communication. Further, the I/F unit 45 transmits and receives various kinds of information to and from an external device through a network using wireless communication or wired communication. Examples of the external device include a radiology information system (RIS) that manages an imaging order and a picture archiving and communication system (PACS).

Furthermore, as described above, the feeding unit 46 is connected to the bus 49. The feeding unit 46 supplies power from the battery 48 to each unit of the mobile radiography apparatus 1. The feeding unit 46 includes, for example, a direct current (DC)-DC converter that converts a direct current voltage from the battery 48 into a voltage having a value corresponding to a supply destination and a voltage stabilizing circuit that stabilizes the value of the converted voltage. The battery 48 according to this embodiment is provided in the main body portion 18 as described above. As described above, the mobile radiography apparatus 1 is wirelessly driven by the battery 48. In addition, a power cord plug (not illustrated) that extends from the bottom of the main body portion 18 in the mobile radiography apparatus 1 can be inserted into an outlet of a commercial power supply to charge the battery 48, or the mobile radiography apparatus 1 can be operated by power from the commercial power supply.

Figure 3:
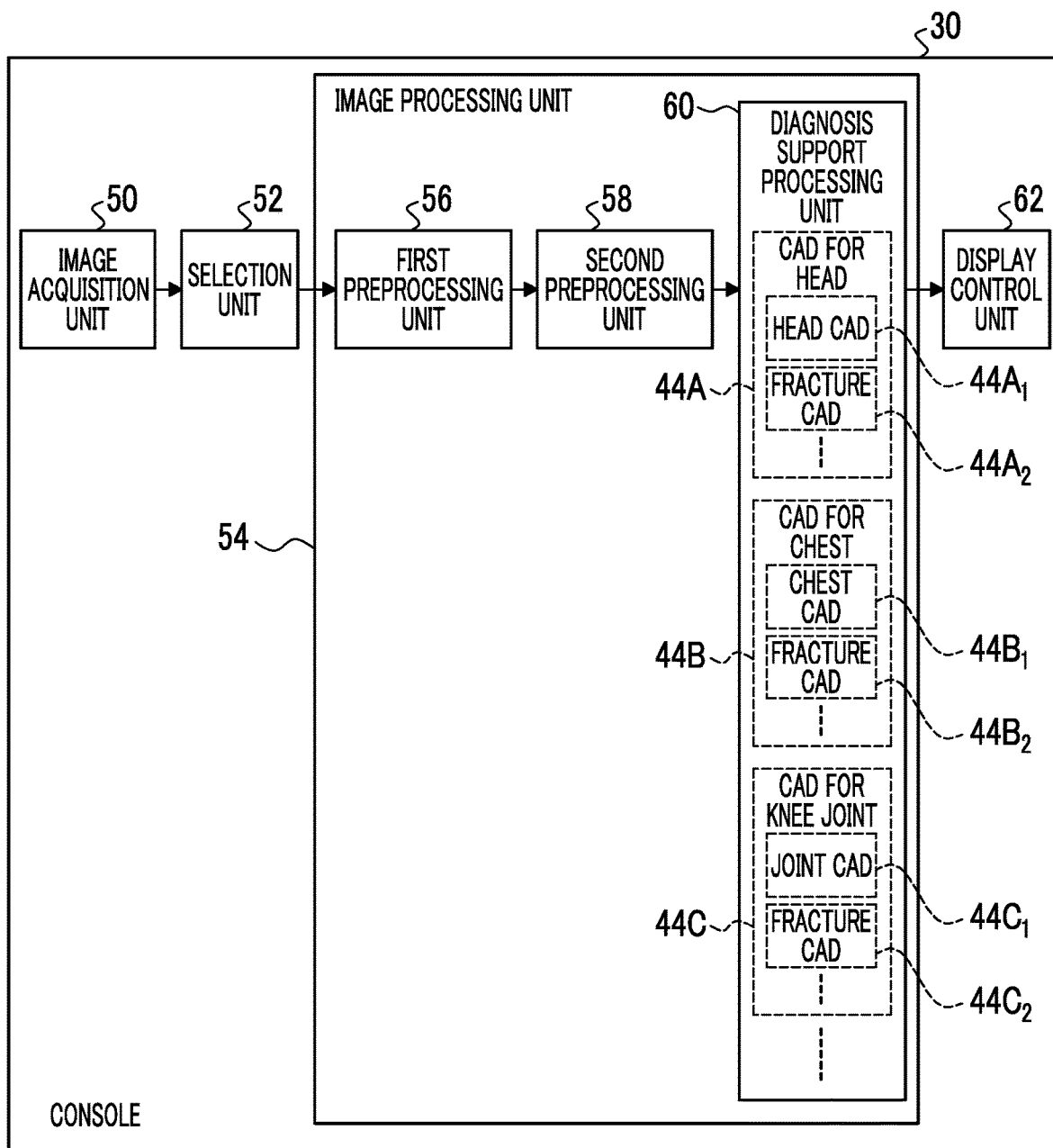
FIG. 3 is a functional block diagram illustrating an example of a configuration related to a function for executing a diagnosis support process in a console according to the embodiment.

Further, the console 30 according to this embodiment has a function of executing the diagnosis support process for the radiographic image captured by the radiation detector 38. FIG. 3 is a functional block diagram illustrating an example of a configuration related to the function of executing the diagnosis support process in the console 30 according to this embodiment. As illustrated in FIG. 3, the console 30 comprises an image acquisition unit 50, a selection unit 52, an image processing unit 54, and a display control unit 62. For example, in the console 30 according to this embodiment, the CPU 32 executes the image processing program 43 stored in the storage unit 42 such that the CPU 32 functions as the image acquisition unit 50, the selection unit 52, and the display control unit 62 and the GPU 34 functions as the image processing unit 54.

The image acquisition unit 50 has a function of acquiring a radiographic image as an image to be processed which is an object to be subjected to the support process. Specifically, as described above, the image acquisition unit 50 according to this embodiment has a function of acquiring image data indicating the radiographic image captured by the radiation detector 38. The image acquisition unit 50 outputs the acquired image data indicating the radiographic image to the selection unit 52. In addition, the console 30 may sequentially acquire the radiographic images captured by the radiation detector 38 or may acquire one or more radiographic images from, for example, the PACS that stores the radiographic images acquired by the radiation detector 38. The image acquisition unit 50 outputs the acquired image data indicating the radiographic image to the selection unit 52.

The selection unit 52 has a function of selecting a support process to be applied to the radiographic image from a plurality of processes of the support process on the basis of a part of the subject that is included in the radiographic image which is the image to be processed acquired by the image acquisition unit 50. First, the selection unit 52 specifies a part of the subject included in the radiographic image. The method by which the selection unit 52 specifies the part of the subject included in the radiographic image is not particularly limited. For example, the selection unit 52 may apply the existing image segmentation technique to the radiographic image to specify the part of the subject included in the radiographic image. In addition, the part of the subject may be defined in advance and is not particularly limited. For example, a part corresponding to the classification of the human body or a part corresponding to each organ or viscera of the human body may be adopted as the part of the subject.

Further, in this embodiment, the support process to be applied for each part of the subject is predetermined. In other words, in this embodiment, the CAD algorithm in the support process applied to the radiographic image is predetermined according to the part of the subject included in the radiographic image. For example, in a case in which the part of the subject included in the radiographic image is the head, it is predetermined that the CAD 44A for the head is applied to the radiographic image. Furthermore, for example, in a case in which the part of the subject included in the radiographic image is the chest, it is predetermined that the CAD 44B for the chest is applied to the radiographic image. Moreover, for example, in a case in which the part of the subject included in the radiographic image is the knee joint, it is predetermined that the CAD 44C for the knee joint is applied to the radiographic image.

Then, the selection unit 52 selects a support process to be applied to the radiographic image from a plurality of processes included in the CAD 44 on the basis of the specified part of the subject. In other words, the selection unit 52 selects an algorithm to be applied to the radiographic image from a plurality of algorithms included in the CAD 44 on the basis of the specified part of the subject. The selection unit 52 outputs the radiographic image input from the image acquisition unit 50 and the selection result to the image processing unit 54.

The image processing unit 54 includes a first preprocessing unit 56, a second preprocessing unit 58, and a diagnosis support processing unit 60. The first preprocessing unit 56 has a function of executing first preprocessing on the radiographic image input from the selection unit 52 before the support process is executed. The radiographic image captured by the radiation detector 38 has a region including a part that needs to be captured for the support process or interpretation. In addition, the radiographic image includes a region other than the region including the necessary part. For example, there is a region that interferes with the interpretation and the like. Therefore, the first preprocessing unit 56 performs trimming for the radiographic image to exclude a region other than the region including the necessary part. Further, the first preprocessing unit 56 can perform the trimming in this way to align the size of the radiographic image or the position of an object of interest in the radiographic image. Furthermore, the region to be trimmed, that is, the region other than the region including the necessary part is predetermined according to the part of the subject included in the radiographic image. The first preprocessing unit 56 performs the trimming in this way to make, for example, the sizes of the images to be subjected to the support process equal to each other for each part. The radiographic image subjected to the first preprocessing is output to the second preprocessing unit 58.

The second preprocessing unit 58 has a function of performing second preprocessing on the radiographic image subjected to the first preprocessing by the first preprocessing unit 56. The second preprocessing is a process for adjusting an image in order to facilitate the interpretation of the radiographic image and is, for example, a gradation process. In addition, the object to which the operator or the interpreter pays attention, such as an organ or a disease, differs depending on the part included in the subject. Therefore, the second preprocessing is also performed according to the part included in the radiographic image. The radiographic image subjected to the second preprocessing is output to the diagnosis support processing unit 60.

The diagnosis support processing unit 60 has a function of executing the support process selected by the selection unit 52 for the radiographic image subjected to the first preprocessing and the second preprocessing to derive the result of the support process. Specifically, the diagnosis support processing unit 60 applies an algorithm corresponding to the support process selected by the selection unit 52 from the algorithms of the CAD 44 to the radiographic image to execute the diagnosis support process.

For example, in a case in which the selection unit 52 specifies that the part of the subject included in the radiographic image is the head, the selection unit 52 selects the CAD 44A for the head as the support process. In this case, the diagnosis support processing unit 60 sequentially applies a plurality of algorithms, such as a head CAD $44A_1$ and a fracture CAD $44A_2$, included in the CAD 44A for the head to the radiographic image to execute the diagnosis support process. Further, for example, in a case in which the selection unit 52 specifies that the part of the subject included in the radiographic image is the chest, the selection unit 52 selects the CAD 44B for the chest as the support process. In this case, the diagnosis support processing unit 60 sequentially applies a plurality of algorithms, such as a chest CAD $44B_1$ and a fracture CAD $44B_2$, included in the chest CAD 44B to the radiographic image to execute the diagnosis support process. Furthermore, for example, in a case in which the selection unit 52 specifies that the part of the subject included in the radiographic image is the knee joint, the selection unit 52 selects the CAD 44C for the knee joint as the support process. In this case, the diagnosis support processing unit 60 sequentially applies a plurality of algorithms, such as a joint CAD $44C_1$ and a fracture CAD $44C_2$, included in the CAD 44C for the knee joint to the radiographic image to execute the diagnosis support process.

In addition, in this embodiment, in a case in which the selected support process includes a plurality of algorithms, such as the CAD 44A for the head, the CAD 44B for the chest, and the CAD 44C for the knee joint, and priority is predetermined, the algorithms are sequentially applied to the radiographic image in the order based on the priority. For example, there may be a disease that the operator wants to preferentially diagnose or treat according to the degree of urgency or the like. In this case, in this embodiment, the priority can be set for the algorithms according to the order in which the support process is preferentially executed. In addition, the priority for the algorithms may be automatically determined on the basis of the general degree of urgency for the disease, or the desired priority may be determined by the operator.

The diagnosis support processing unit 60 outputs the obtained result of the support process to the display control unit 62.

The display control unit 62 has a function of displaying the result of the support process by the diagnosis support processing unit 60 on the display unit 36.

Figure 4:
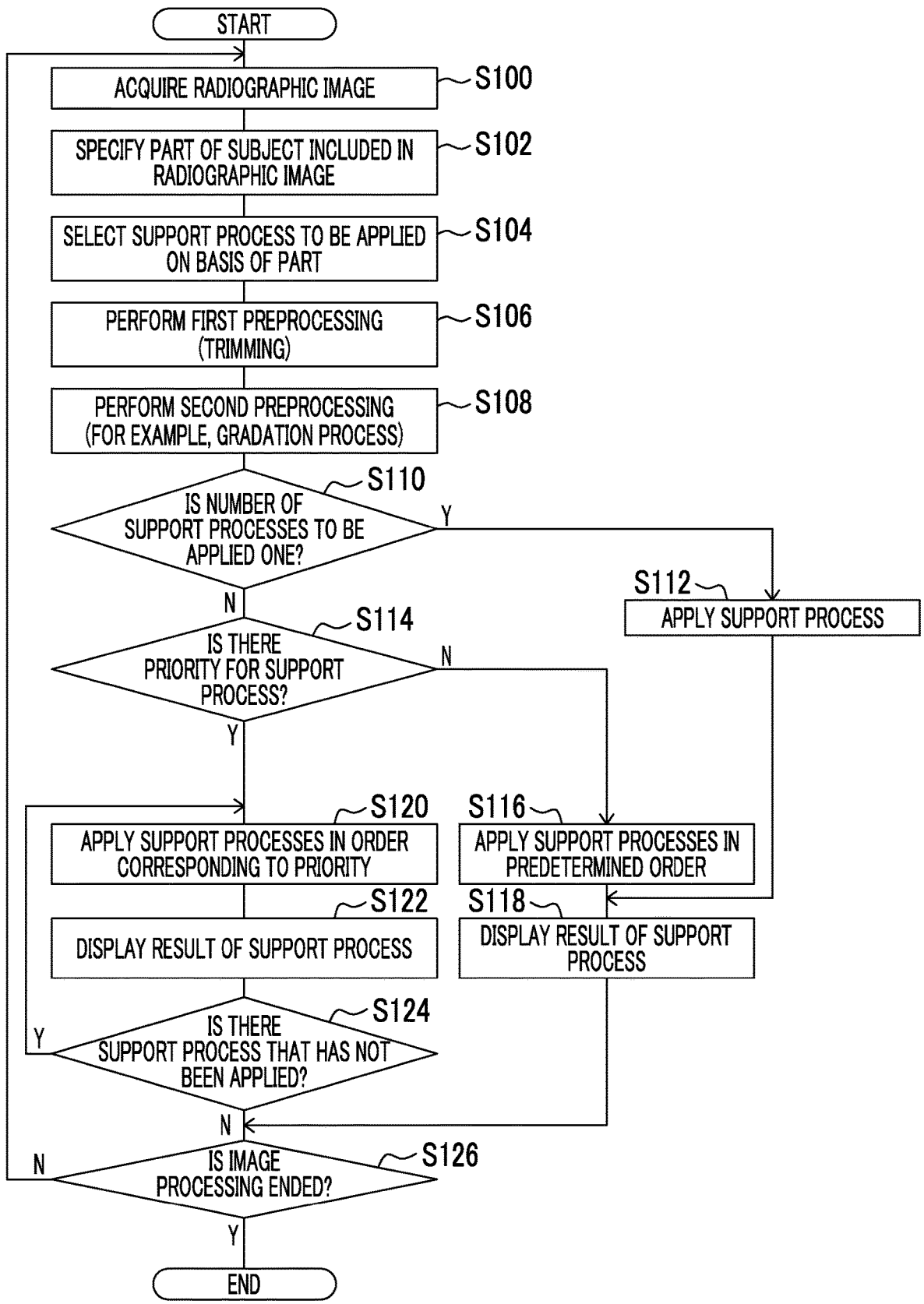
FIG. 4 is a flowchart illustrating an example of the flow of image processing by the console according to the embodiment.

Next, the operation of the console 30 related to the diagnosis support process will be described with reference to the drawings. FIG. 4 is a flowchart illustrating an example of the flow of the image processing performed by the console 30 according to this embodiment. For example, in the console 30 according to this embodiment, in a case in which a diagnosis support process execution instruction input by the operator through the operation unit 37 is receives or in a case in which the time predetermined as an execution cycle of the diagnosis support process comes, the CPU 32 executes the image processing program 43 stored in the storage unit 42 to perform the image processing whose example is illustrated in FIG. 4.

In Step S100 of FIG. 4, the image acquisition unit 50 acquires a radiographic image which is the image to be processed. In addition, in a case in which there are a plurality of images to be processed, the image acquisition unit 50 acquires one of the images.

Figure 5:
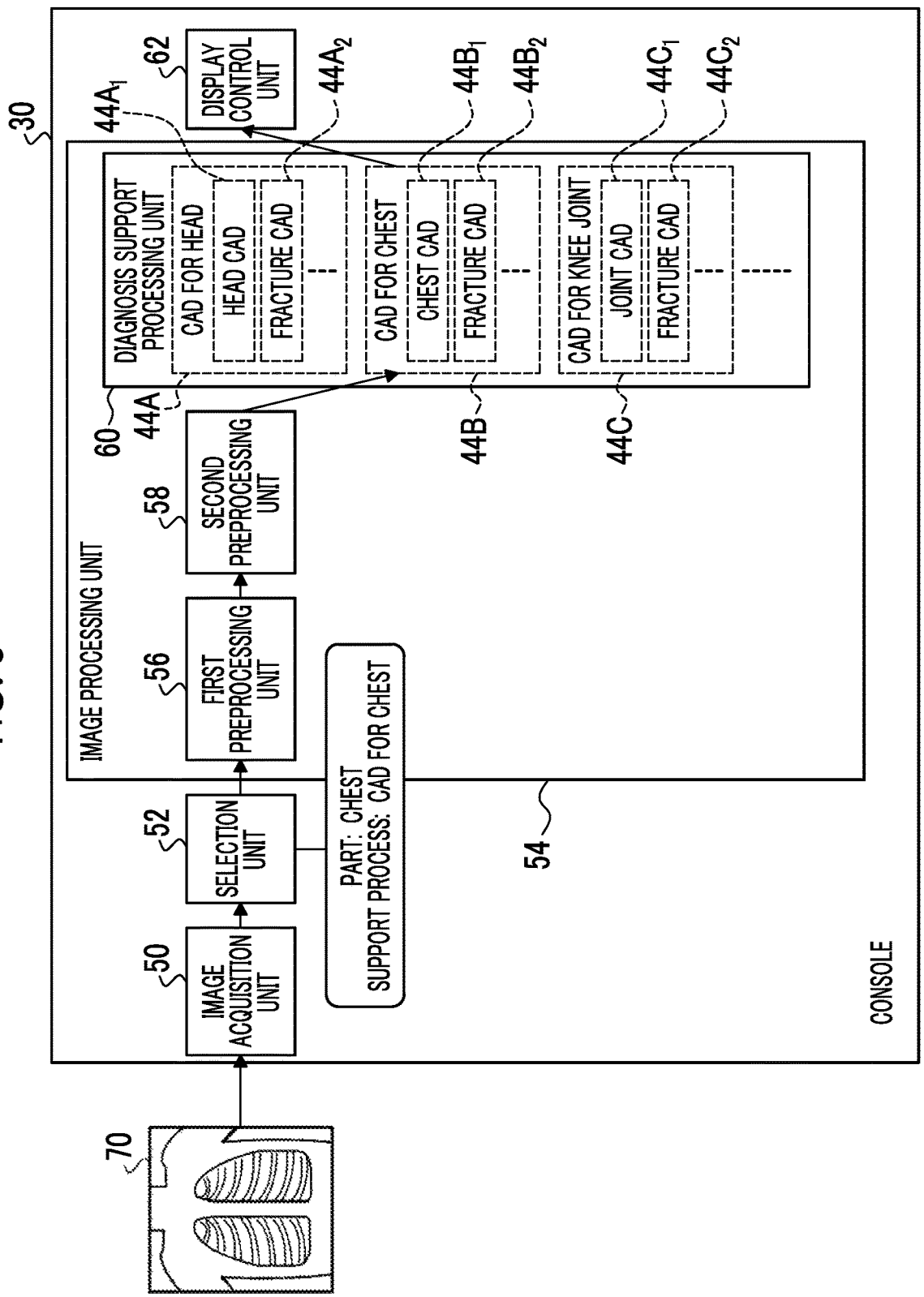
FIG. 5 is a diagram illustrating the image processing by the console.

Then, in Step S102, the selection unit 52 specifies a part of the subject included in the radiographic image acquired in Step S100 as described above. Then, in Step S104, the selection unit 52 selects the support process to be applied to the radiographic image on the basis of the part of the subject specified in Step S102 as described above. For example, as illustrated in FIG. 5, in a case in which the image acquisition unit 50 acquires a radiographic image 70 obtained by imaging the chest of the subject in Step S100, the selection unit 52 specifies the "chest" as the part of the subject included in the radiographic image in Step S102. Further, the selection unit 52 selects the CAD 44B for the chest as the support process applied to the radiographic image in Step S104.

Then, in Step S106, the first preprocessing unit 56 performs the first preprocessing for the radiographic image acquired in Step S100. Specifically, as described above, the first preprocessing unit 56 performs trimming according to the part specified in Step S102 for the radiographic image.

Then, in Step S108, the second preprocessing unit 58 performs the second preprocessing for the radiographic image subjected to the first preprocessing in Step S106. Specifically, as described above, the second preprocessing unit 58 performs a process for adjusting an image to facilitate the interpretation of a radiographic image, such as a gradation process, for the radiographic image according to the part specified in Step S102.

Then, in Step S110, the diagnosis support processing unit 60 determines whether or not the number of support processes applied to the radiographic image selected in Step S104 is one. Specifically, in a case in which the number of algorithms applied to the radiographic image is one, the determination result in Step S110 is "Yes", and the process proceeds to Step S112. In Step S112, the diagnosis support processing unit 60 applies the support process selected in Step S104 to the radiographic image and then proceeds to Step S118.

On the other hand, for example, as illustrated in FIG. 5, in a case in which the CAD 44B for the chest is selected as the support process to be applied to the radiographic image 70, the CAD 44B for the chest includes a plurality of algorithms such as the chest CAD $44B_1$ and the fracture CAD $44B_2$. Therefore, the number of support processes applied to the radiographic images, specifically, the number of algorithms is two or more. Therefore, the determination result in Step S110 is "Yes", and the process proceeds to Step S114.

In Step S114, the diagnosis support processing unit 60 determines whether or not the priority is predetermined for the plurality of support processes (algorithms) to be applied. As described above, in a case in which the priority is predetermined for the plurality of support processes to be applied, the determination result in Step S114 is "Yes", and the process proceeds to Step S120.

In Step S120, the diagnosis support processing unit 60 applies the support processes to the radiographic image in the order corresponding to the priority. Specifically, the diagnosis support processing unit 60 applies one support process corresponding to the priority among the plurality of support processes (algorithms) to be applied to the radiographic image to execute the diagnosis support process and outputs the result of the support process to the display control unit 62.

Then, in Step S122, the display control unit 62 displays the result of the support process in Step S120 on the display unit 36. In addition, the display mode of the result of the support process by the display control unit 62 is not particularly limited. For example, whenever the result of the support process is output, the display control unit 62 may display, on the display unit 36, the results of the support processes side by side or so as to be switchable.

Then, in Step S124, the diagnosis support processing unit 60 determines whether or not there is a support process that has not yet been applied (not applied) among the plurality of support processes (algorithms) to be applied. In the example illustrated in FIG. 5, the chest CAD $44B_1$ is applied to the radiographic image 70 to obtain the result of the support process. In a case in which the fracture CAD $44B_2$ has not yet been applied, there is a support process that has not been applied. Therefore, the determination result in Step S124 is "Yes", and the process returns to Step S120. Then, the processes in Steps S120 and S122 are repeated. On the other hand, in a case in which there is no support process that has not been applied, the determination result in Step S124 is "No", and the process proceeds to Step S126.

As described above, in this embodiment, in a case in which the priority is determined for the plurality of support processes to be applied, the results of the support processes are sequentially displayed on the display unit 36 as soon as the results of the support processes are obtained. Therefore, even in a state in which the results of all of the support processes are not obtained, it is possible to present the results of the support processes that have already been obtained. As a result, for example, it is possible to promptly present the results of the support processes with a high degree of urgency to the operator.

On the other hand, in Step S114, in a case in which the priority is not predetermined for the plurality of support processes to be applied, the determination result is "No", and the process proceeds to Step S116. In Step S116, the display control unit 62 applies the support processes to the radiographic image in a predetermined order. In the process of this step, all of the plurality of support processes to be applied are sequentially applied to the radiographic image, and all of the results of the support processes are output to the display control unit 62 unlike Step S120.

Then, in Step S118, the display control unit 62 displays all of the results of the support processes obtained in Step S116 on the display unit 36 and then proceeds to Step S126. In addition, the display mode of the result of the support process by the display control unit 62 is not particularly limited. For example, the display control unit 62 may display, on the display unit 36, the results of the support processes side by side or so as to be switchable.

Figure 6:
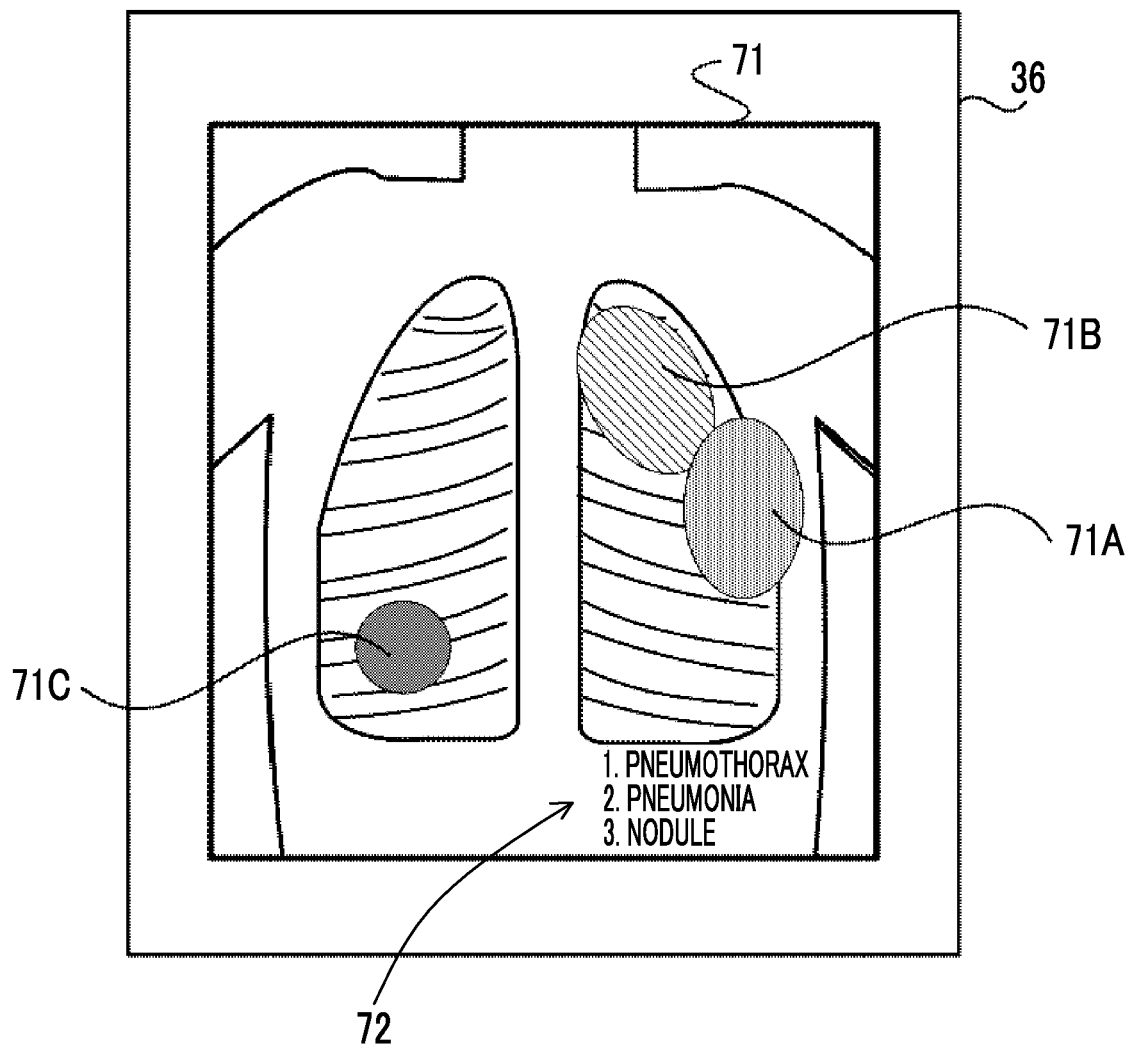
FIG. 6 is a diagram illustrating an example of a display mode in which a display control unit displays a support process result on a display unit.

In addition, in a case in which the priority to which the operator pays attention is set to the results of the support processes according to, for example, the degree of urgency, the display control unit 62 may present the results of the support processes in an order based on the priority. For example, in a case in which the support processing unit 64 executes the support process for each of a plurality of lesions according to the part, the display control unit 62 may display the results of the support processes on the display unit 36 in an order based on the priority set for the plurality of lesions. FIG. 6 illustrates an example of a display mode in which the display control unit 62 displays the results of the support processes on the display unit 36 in a case in which the CAD 44B for the chest is applied to each of a plurality of lesions, such as pneumothorax, pneumonia, and a nodule, for which the priority has been set, for the radiographic image of the chest of the subject. In a support process result 71 illustrated in FIG. 6, a plurality of lesions of pneumothorax 71A, pneumonia 71B, and a nodule 71C are extracted. In addition, the support process result 71 includes priority information 72 indicating the order based on the priority set for the "pneumothorax", the "pneumonia", and the "nodule". This configuration which presents the support process results according to the priority makes it easier to see the lesion of interest.

In Step S126, the display control unit 62 determines whether or not to end the image processing illustrated in FIG. 4. In a case in which there are a plurality of images to be processed and there is an image to be processed which has not yet been subjected to the support process, the determination result in Step S126 is "No", and the process returns to Step S100. Then, the processes in Steps S100 to S124 are repeated. On the other hand, in a case in which there is no image to be processed which has not yet been subjected to the support process, the determination result in Step S126 is "Yes", and the image processing illustrated in FIG. 4 ends.

As described above, in the console 30 of the mobile radiography apparatus 1 according to the above-described embodiment, the CPU 32 acquires the image to be processed which is the object to be subjected to the support process that is the diagnosis support process or the imaging support process and selects a support process to be applied to the image to be processed from a plurality of processes of the support process on the basis of the part of the subject included in the image to be processed.

In a case in which different support processes are applied to the image to be processed for each part of the subject included in the image to be processed, for example, the operator needs to check each part of the subject included in the image to be processed and to apply the support process. As a result, the burden on the user increases. In this case, the console 30 according to the above-described embodiment selects a support process to be applied to the image to be processed from a plurality of processes of the support process on the basis of the part of the subject included in the image to be processed. Therefore, it is possible to apply an appropriate support process to the image to be processed, without bothering the operator. In particular, at the scene of emergency, a plurality of images to be processed may be captured for a plurality of parts. According to the console 30 of the above-described embodiment, it is possible to automatically apply an appropriate support process to each of a plurality of images to be processed which include various parts of the subject. Therefore, according to the console 30 of the above-described embodiment, it is possible to reduce the burden on the operator.

Further, in the above-described embodiment, the aspect in which the GPU 34 functions as the diagnosis support processing unit 60 and executes the diagnosis support process for the radiographic image has been described. That is, the aspect mode in which the radiographic image is applied as an example of the image to be processed according to the present disclosure and the diagnosis support process is applied as an example of the support process according to the present disclosure has been described. However, the present disclosure is not limited to this aspect. For example, the support process may be an imaging support process for supporting the capture of a radiographic image by the mobile radiography apparatus 1. An example of the imaging support process is a positioning support process for supporting the positioning of the subject. Further, the image to be processed may be a visible light image captured by a visible light camera, a distance image captured by a depth camera, or the like. In addition, the depth camera is, for example, a camera that captures a distance image composed of pixels having distance information indicating the distance to an object to be imaged, using a time-of-flight (TOF) method. Furthermore, the image to be processed may be a medical image, such as a computed tomography (CT) image or an ultrasound image.

In addition, in the above-described embodiment, the aspect in which the mobile radiography apparatus having the C-arm is applied as an example of the medical imaging apparatus that captures a radiographic image has been described. However, the medical imaging apparatus is not limited to this embodiment. For example, a combination of a mobile cart having the radiation emitting unit 10 and the radiation detector 38 which is a so-called electronic cassette may be used as the medical imaging apparatus. Further, for example, a portable medical imaging apparatus that the operator carries and moves may be used. Furthermore, the imaging apparatus is not limited to the mobile medical imaging apparatus and may be a stationary medical imaging apparatus. Moreover, it is possible to use an imaging apparatus corresponding to the image to be processed.

In addition, in the above-described embodiment, the aspect in which the diagnosis support processing unit 60 applies the CAD algorithm to execute the diagnosis support process has been described. However, the aspect in which the diagnosis support process is executed or the CAD is not limited to this embodiment. For example, the diagnosis support processing unit 60 may apply artificial intelligence (AI) technology to execute the diagnosis support process or may apply a trained model, which has been machine-trained by deep learning or the like, to execute the diagnosis support process.

Further, in the above-described embodiment, the aspect in which the console 30 is an example of the image processing device according to the present disclosure has been described. However, devices other than the console 30 may have the functions of the image processing device according to the present disclosure. In other words, a device other than the console 30 may comprise some or all of the image acquisition unit 50, the selection unit 52, the image processing unit 54, and the display control unit 62. For example, the CPU 32 that functions as the console 30 and the GPU 34 and the storage unit 42 that function as the image processing unit 54 may be separately provided, or the GPU 34 may be provided as a so-called GPU box.

In addition, in the above-described embodiment, for example, the following various processors can be used as a hardware structure of processing units performing various processes, such as the image acquisition unit 50, the selection unit 52, the image processing unit 54, and the display control unit 62. The various processors include, for example, a CPU which is a general-purpose processor executing software (programs) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the image processing program 43 is stored (installed) in the storage unit 42 in advance has been described. However, the present disclosure is not limited thereto. The image processing program 43 may be recorded on a recording medium, such as a compact disc read only memory (CD-ROM), a digital versatile disc read only memory (DVD-ROM), or a universal serial bus (USB) memory, and then provided. In addition, the image processing program 43 may be downloaded from an external device through a network.

What is claimed is:

1. A medical imaging apparatus comprising:
a radiation source that emits radiation;
a radiation detector that detects the radiation and generates a radiographic image; and
an image processing device including at least one processor,
wherein the processor acquires the radiographic image from the radiation detector as an image to be processed, which is an object to be subjected to a support process that is a diagnosis support process or an imaging support process, and the processor selects the support process to be applied to the image to be processed from a plurality of support processes based on a part of a subject which is included in the image to be processed,
wherein the processor executes the support process according to the part of the subject, and the processor displays results of the executed support process on a display,
wherein the plurality of support processes include a plurality of algorithms for each part of the subject, and a priority is set for the plurality of algorithms, and
wherein, in a case in which the plurality of algorithms are applied to the image to be processed, the processor applies the plurality of algorithms to the image to be processed in an order based on the priority.

2. The medical imaging apparatus according to claim 1, wherein the processor applies the selected support process to the image to be processed and outputs a support process result.

3. The medical imaging apparatus according to claim 1, wherein the processor executes the support process for each of a plurality of lesions according to the part and presents the support process results in an order based on the priority set for the plurality of lesions.

4. The medical imaging apparatus according to claim 1, wherein the processor trims the image to be processed on the basis of the part and applies the support process to the trimmed image to be processed.

5. A mobile medical imaging apparatus comprising:
the medical imaging apparatus according to claim 1; and
a power source that supplies power to the processor of the image processing device.

6. An image processing method that is executed by a computer, the image processing method comprising:
acquiring a radiographic image from a radiation detector as an image to be processed, which is an object to be subjected to a support process that is a diagnosis support process or an imaging support process; and
selecting the support process to be applied to the image to be processed from a plurality of support processes based on a part of a subject which is included in the image to be processed,
executing the support process according to the part of the subject and displaying results of the executed support process on a display,
wherein the plurality of support processes include a plurality of algorithms for each part of the subject, and a priority is set for the plurality of algorithms, and
wherein, in a case in which the plurality of algorithms are applied to the image to be processed, the plurality of algorithms are applied to the image to be processed in an order based on the priority.

7. A non-transitory computer-readable storage medium storing an image processing program that causes a computer to execute a process comprising:
acquiring a radiographic image from a radiation detector as an image to be processed, which is an object to be subjected to a support process that is a diagnosis support process or an imaging support process; and
selecting the support process to be applied to the image to be processed from a plurality of support processes based on a part of a subject which is included in the image to be processed,
executing the support process according to the part of the subject and displaying results of the executed support process on a display,
wherein the plurality of support processes include a plurality of algorithms for each part of the subject, and a priority is set for the plurality of algorithms, and
wherein, in a case in which the plurality of algorithms are applied to the image to be processed, the plurality of algorithms are applied to the image to be processed in an order based on the priority.

* * * * *